United States Patent [19]

Maierhofer et al.

[11] 4,129,593

[45] Dec. 12, 1978

[54] PROCESS FOR THE PRODUCTION OF HIGH PURITY S-CARBOXYMETHYL-L-CYSTEINE

[75] Inventors: Alfred Maierhofer, Allensbach; Hans Wagner, Kostanz, both of Germany

[73] Assignee: Deutsche Gold- und Silber-Scheideanstalt vormals Roessler, Frankfurt, Germany

[21] Appl. No.: 833,043

[22] Filed: Sep. 14, 1977

[30] Foreign Application Priority Data

Oct. 19, 1976 [DE] Fed. Rep. of Germany ....... 2647094

[51] Int. Cl.$^2$ .......................................... C07C 101/20
[52] U.S. Cl. ...................................... 562/557; 560/153
[58] Field of Search .......................... 260/534 E, 534 S; 560/195, 153

[56] References Cited

U.S. PATENT DOCUMENTS

| | | | |
|---|---|---|---|
| 2,460,785 | 2/1949 | Pierson et al. | 260/534 S |
| 3,184,505 | 5/1965 | Martin et al. | 260/534 S |

OTHER PUBLICATIONS

Berezovskii, V. M. et al. "Synthesis of Substituted 3-Ketothiophanes by Dieckmann Cyclization" J. Gen. Chem. U.S.S.R. (1963) pp. 2815–2820.

Greenstein, Jessie P. et al. "Chemistry of the Amino Acids" vol. 3 (1961) p. 1901, Wiley Publ.

Mellor, J. W. "Inorganic and Theoretical Chemistry", vol. 10 (1949) p. 171, Longmans, Green & Co. Publ.

Kirk-Othmer "Encyclopedia of Chemical Technology" 2nd Ed. vol. 10, pp. 100 and 102, Interscience Publ.

*Primary Examiner*—James O. Thomas, Jr.
*Assistant Examiner*—Leah Hendriksen
*Attorney, Agent, or Firm*—Cushmn, Darby & Cushman

[57] ABSTRACT

Very pure S-carboxymethyl-L-cysteine is prepared by reacting L-cystine in liquid ammonia with metallic sodium to form the disodium salt of L-cysteine, evaporating the ammonia, reacting the disodium salt of L-cysteine with an aqueous solution of chloroacetic acid and precipitating the S-carboxymethyl-L-cysteine formed by acidifying the reaction mixture. There is employed 0.1 to 10 weight percent of a reducing agent based on the chloroacetic acid.

12 Claims, No Drawings

PROCESS FOR THE PRODUCTION OF HIGH PURITY S-CARBOXYMETHYL-L-CYSTEINE

BACKGROUND OF THE INVENTION

The invention is directed to a process for the production of very pure S-carboxymethyl-L-cysteine by reacting L-cystine in liquid ammonia with metallic sodium to form the disodium salt of L-cysteine, vaporizing the ammonia, reacting the disodium salt of L-cysteine with an aqueous solution of chloracetic acid and precipitating the S-carboxymethyl-L-cysteine formed by acidifying the reaction mixture.

A process of this type is described in Zhurnal Obshchei Khimii, Vo. 33 No. 9 pages 2888 to 2894. However, in the known process even if one works with the complete exclusion of air and pays attention to the reduction of the L-cystine employed proceeding quantitatively products are always obtained which contain up to 2 weight percent of L-cystine whose subsequent removal creates considerable difficulties because of the difficult solubility in water.

S-carboxymethyl-L-cysteine (SCC) is of pharmaceutical interest since it has mucous dissolving properties. Viscous mucous is rendered thin liquid by SCC and can thereby be more easily eliminated by coughings. Breathing is improved and made easier. SCC therefore is used for the production of medicines for treatment of bronchitis, tuberculosis, asthmatic illnesses as well as inflammations in the region of the throat and windpipe.

Since especially high purity requirements must be placed on pharmaceutical products the problem must be solved by the present invention of producing a very pure S-carboxymethyl-L-cysteine which is particularly free from L-cystine.

SUMMARY OF THE INVENTION

The process of the invention is characterized by the reaction of the disodium salt of L-cysteine with an aqueous solution of chloroacetic acid taking place in the presence of 0.1 to 10 weight percent, based on the chloroacetic acid of a reducing agent.

By the process of the invention there is produced a highly pure SCC in very high yield and completely free from L-cystine.

Preferably the reducing agent is used in an amount of 1 to 5 weight percent based on the weight of chloroacetic acid employed.

Especially suited reducing agents are the alkali salts of oxygen containing acids of sulfur at a lower stage of oxidation, e.g., the corresponding dithionites, sulfoxylates or pyrosulfites and formic acid. Examples of such salts are sodium dithionite, potassium dithionite, sodium pyrosulfite and potassium pyrosulfite. There can also be used sodium bisulfite and potassium bisulfite for example.

The reaction of L-cystine in liquid ammonia with metallic sodium suitably takes place at a temperature from $-60°$ to $+20°$ C. Especially advantageous are temperatures from $-5°$ to $+10°$ C., on the one hand to save cold energy and on the other to avoid too high pressures.

Although the stoichiometric amount of four moles of metallic sodium should be sufficient for reaction with one mole of L-cystine it has proven advantageous to add the sodium in a molar excess of about 5 to 10%. The reaction is complete when the blue color brought about by the excess of elemental sodium remains. The unreacted sodium then after the end of the reaction is destroyed by ammonium chloride of methanol.

The ammonia is vaporized, suitably at normal pressure (i.e., atmospheric pressure) and can be recovered for renewed use. The disodium salt of L-cysteine remaining behind is taken up in water and reacted with an aqueous solution of chloroacetic acid which simultaneously contains the reducing agent. The reaction takes place suitably at a temperature of $+20°$ to $100°$ C., preferably at a temperature of $30°$ to $50°$ C. The reaction generally requires a time of about one hour. To produce higher yields of SCC it is advantageous to use the chloroacetic acid in a molar excess of about 15 to 25%. The concentration of chloroacetic acid in water is not critical, but usually is between 100 and 600 grams/liter.

When the reaction of the disodium salt of L-cysteine with the chloroacetic acid is ended the reaction mixture is cooled to room temperature and is adjusted with a mineral acid, for example hydrochloric acid to a pH of about 2.5 to 3.0. The particular acid is not critical. Other suitable acids include hydrobromic acid and sulfuric acid. Upon establishment of the pH of 2.5 to 3.0 the desired SCC separates out. It is centrifuged and dried in a vacuum at $70°$ to $90°$ C.

For the production of higher yields it is suitable to carry out all operations with the exclusion of air, for example in a nitrogen or other inert atmosphere.

In the following examples the rotary power of the S-carboxymethyl-L-cysteine is given as specific rotation $\alpha_D^{20}$ in degrees . $cm^3$/dm ·g. Percent data unless otherwise indicated is always percent by weight.

The process can comprise, consist essentially of or consist of the steps set forth using the recited materials.

DESCRIPTION OF THE PREFERRED EMBODIMENTS

EXAMPLE 1

There were placed 120 grams of L-cystine (0.5 mole) in a 2 liter three-necked flask equipped with a stirrer thermometer and methanol/dry ice cooling and 1.5 liters of liquid ammonia were allowed to enter at $-40°$ C. Then there were added under continuous cooling 50 grams (2.17 moles) of sodium metal in portions of 1 to 2 grams during the course of one hour. The end of the reaction was recognized by the continuation of the blue color. After the end of the reaction the excess sodium was destroyed by the addition of ammonium chloride and the ammonia vaporized at normal pressure. The residue was taken up in 500 ml of water and concentrated in a vacuum to 200 ml in order to remove residual ammonia, and again treated with 300 ml of water. The entire operations were carried out under a nitrogen atmosphere.

The aqueous solution of the disodium salt of L-cysteine obtained is then reacted at $20°$ to $30°$ C. under a nitrogen atmosphere in the course of 30 minutes with stirring with a solution of 104 grams of chloroacetic acid (1.1 moles) and 4 grams of sodium pyrosulfite in 200 ml of water. It is also allowed to post react for 15 minutes at $20°$ C., the solution clarified over activated carbon and the filtrate treated with 90 ml of concentrated hydrochloric acid to a pH of 2.5. Thereby the S-carboxymethyl-L-cysteine precipitates out in crystalline form. The product is filtered off with suction, well stirred in 500 ml of water, again filtered with suction and dried in a vacuum at $70°$ C.

Yield: 165 grams ≙ 92% theory based on L-cystine, Specific rotation $\alpha_D^{20}$: −35.7 (concentration = 10% in 1N NaOH at pH 6): Content of SCC 99.5%: Thin layer chromatograph homogeneous, free of L-cystine.

EXAMPLE 2

400 grams of L-cystine (1.67 moles) were present in a 5 liter double-jacketed stainless steel autoclave equipped with a pressure lock and brine cooling, the autoclave tightly closed and there were filled in 3.5 liters of liquid ammonia from a steel flask. In the course of 2 hours there were added 190 grams of sodium metal (8.26 moles) via the pressure lock and the reaction temperature during the course of the brine cooling held at +5° C. The pressure was 4 to 6 bars and was held at this height by occasional opening of a pressure reduction valve. After the end of the reaction the excess sodium was destroyed by addition of 20 ml of methanol and the remaining colorless suspension subjected to super atmospheric pressure in a second 5 liter stirrer equipped autoclave which contained 3000 ml of water. Thereby the greater part of the ammonia escaped via a pressure reduction valve. The aqueous solution obtained was then concentrated to 1000 ml and again treated with 3000 ml of water. The last named operation was carried out under a nitrogen atmosphere.

The aqueous solution of the disodium salt of L-cysteine obtained was reacted with a solution of 346 grams of chloroacetic acid (3.66 moles) and 20 grams of formic acid in 700 ml of water in the manner described in Example 1.

Yield: 565 grams = 94.5% of theory based on L-cystine; $\alpha_D^{20}$: −35.7°; Content of SCC 99.5%. Thin layer chromatograph: homogeneous, free from cystine.

What is claimed is:

1. In a process for the production of highly pure S-carboxymethyl-L-cysteine by reacting L-cystine in liquid ammonia with metallic sodium to form the disodium salt of L-cysteine, vaporizing the ammonia, reacting the disodium salt of L-cysteine with an aqueous solution of chloroacetic acid and precipitating the S-carboxymethyl-L-cysteine formed by acidifying the reaction mixture, the improvement comprising carrying out the reaction of the disodium salt of L-cysteine with aqueous chloroacetic acid in the presence of 0.1 to 10 weight percent based on the chloroacetic acid of a reducing agent which is formic acid or an alkali salt of an oxygen containing acid of sulfur wherein the sulfur has a valance below 6, all steps of the process being carried out with the exclusion of air.

2. The process of claim 1 wherein there is employed 1 to 5 weight percent of the reducing agent.

3. The process of claim 2 wherein there is employed as the reducing agent an alkali salt of an oxygen containing acid of sulfur wherein the sulfur has a valence below 6.

4. The process of claim 2 wherein the reducing agent is formic acid.

5. The process of claim 1 wherein the reducing agent is an alkali salt of an oxygen containing acid of sulfur wherein the sulfur has a valence below 6.

6. The process of claim 5 wherein the reducing agent is an alkali dithionite or alkali pyrosulfite.

7. The process of claim 5 wherein the reducing agent is an alkali sulfite.

8. The process of claim 1 wherein the reducing agent is formic acid.

9. The process of claim 1 wherein the amount of chloroacetic acid is from 1 to 1.25 moles per mole of the disodium salt of L-cysteine.

10. The process of claim 9 wherein the amount of chloroacetic acid is 1.15 to 1.25 moles per mole of the disodium salt of L-cysteine.

11. The process of claim 1 wherein the process is carried out in an inert atmosphere.

12. The process of claim 11 wherein the inert atmosphere is nitrogen.